United States Patent
Chen et al.

(10) Patent No.: US 9,864,091 B2
(45) Date of Patent: Jan. 9, 2018

(54) CT SECURITY INSPECTION SYSTEM FOR BAGGAGE AND DETECTOR ARRANGEMENT THEREOF

(71) Applicant: NUCTECH COMPANY LIMITED, Beijing (CN)

(72) Inventors: Zhiqiang Chen, Beijing (CN); Yuanjing Li, Beijing (CN); Li Zhang, Beijing (CN); Jinyu Zhang, Beijing (CN); Zhanjun Duan, Beijing (CN); Longsong Ran, Beijing (CN); Qingping Huang, Beijing (CN)

(73) Assignee: NUCTECH COMPANY LIMITED, Beijing (CN)

( * ) Notice: Subject to any disclaimer, the term of this patent is extended or adjusted under 35 U.S.C. 154(b) by 234 days.

(21) Appl. No.: 14/355,240

(22) PCT Filed: Jul. 15, 2013

(86) PCT No.: PCT/CN2013/079381
§ 371 (c)(1),
(2) Date: Apr. 30, 2014

(87) PCT Pub. No.: WO2014/044078
PCT Pub. Date: Mar. 27, 2014

(65) Prior Publication Data
US 2014/0314200 A1   Oct. 23, 2014

(30) Foreign Application Priority Data
Sep. 19, 2012   (CN) .......................... 2012 1 0350516

(51) Int. Cl.
*G01V 5/00*   (2006.01)
*G01N 23/04*   (2006.01)
(Continued)

(52) U.S. Cl.
CPC .............. *G01V 5/005* (2013.01); *A61B 6/032* (2013.01); *A61B 6/035* (2013.01); *G01N 23/046* (2013.01); *G01V 5/0016* (2013.01); *G01V 5/0041* (2013.01)

(58) Field of Classification Search
CPC .... G01V 5/0016; G01V 5/0041; G01V 5/005; A61B 6/032; A61B 6/035; G01N 23/046
(Continued)

(56) References Cited

U.S. PATENT DOCUMENTS

| 4,115,696 A | 9/1978 | Truscott |
| 4,315,157 A * | 2/1982 | Barnes .................. A61B 6/032 378/10 |

(Continued)

FOREIGN PATENT DOCUMENTS

| CN | 1708686 A | 12/2005 |
| CN | 101400992 A | 4/2009 |

(Continued)

OTHER PUBLICATIONS

State Intellectual Property Office of the People's Republic of China, Second Office Action in Chinese Application No. 201210350516.X (dated Nov. 23, 2015).
(Continued)

*Primary Examiner* — Allen C. Ho
(74) *Attorney, Agent, or Firm* — Leydig, Voit & Mayer, Ltd.

(57) ABSTRACT

The present invention discloses a CT security inspection system for baggage. The CT security inspection system comprises a scanning passage through which a baggage enters and exits the CT security inspection system for baggage, an X-ray source provided at one side of the scanning passage, and, a gantry provided at an opposite side of the scanning passage, and on which a plurality of detector
(Continued)

units are mounted. In each of the detector units, a vertex point of at least one detector unit is positioned in a detector unit distribution circle with its center at a center of the scanning passage, and the detector units are arranged successively. All the detector crystal receiving faces of the plurality of detector units are within a scope of radiating ray beams with their center at the target of the X-ray source. In each of the detector units, a connection line between a midpoint of at least one of the detector crystal receiving faces and the target of the X-ray source is normal to the corresponding detector crystal receiving face.

19 Claims, 3 Drawing Sheets

(51) Int. Cl.
G01N 23/08 (2006.01)
G01N 23/083 (2006.01)
G01N 23/087 (2006.01)
A61B 6/03 (2006.01)

(58) Field of Classification Search
USPC ............... 378/19, 57, 98.8; 250/370.09
See application file for complete search history.

(56) References Cited

U.S. PATENT DOCUMENTS

| | | | | |
|---|---|---|---|---|
| 4,751,644 A * | 6/1988 | Koka | A61B 6/032 | 378/14 |
| 4,843,618 A * | 6/1989 | Best | A61B 6/032 | 378/4 |
| 5,008,907 A * | 4/1991 | Norman | A61B 6/032 | 378/17 |
| 5,025,463 A * | 6/1991 | Saito | A61B 6/032 | 378/19 |
| 5,029,192 A * | 7/1991 | Schwierz | A61B 6/035 | 378/11 |
| 5,031,198 A * | 7/1991 | Deucher | A61B 6/035 | 378/15 |
| 5,058,011 A * | 10/1991 | Nagai | G06T 11/005 | 378/13 |
| 5,166,961 A * | 11/1992 | Brunnett | A61B 6/032 | 378/116 |
| 5,208,746 A * | 5/1993 | King | A61B 6/027 | 378/14 |
| 5,262,946 A * | 11/1993 | Heuscher | A61B 6/032 | 378/15 |
| 5,396,418 A * | 3/1995 | Heuscher | A61B 6/032 | 378/15 |
| 5,481,583 A * | 1/1996 | Heuscher | G06F 17/153 | 378/4 |
| 5,544,212 A * | 8/1996 | Heuscher | A61B 6/032 | 378/15 |
| 5,668,851 A * | 9/1997 | Dobbs | A61B 6/4291 | 378/154 |
| 5,712,889 A | 1/1998 | Lanzara et al. | | |
| 5,757,878 A * | 5/1998 | Dobbs | A61B 6/032 | 378/19 |
| 5,757,951 A * | 5/1998 | Tuy | G06T 11/005 | 378/4 |
| 5,781,606 A * | 7/1998 | Dobbs | A61B 6/032 | 378/19 |
| 5,818,897 A * | 10/1998 | Gordon | G01V 5/005 | 378/19 |
| 5,912,938 A * | 6/1999 | Dobbs | G01N 23/046 | 378/19 |
| 5,982,845 A * | 11/1999 | Sidoti | G06T 11/006 | 378/4 |
| 6,078,639 A * | 6/2000 | Heuscher | G06T 11/006 | 378/15 |
| 6,097,784 A * | 8/2000 | Tuy | G06T 11/005 | 378/15 |
| 6,104,775 A * | 8/2000 | Tuy | G06T 11/005 | 378/15 |
| 6,154,516 A * | 11/2000 | Heuscher | A61B 6/032 | 378/15 |
| 6,163,617 A * | 12/2000 | Heuscher | G06T 11/006 | 382/132 |
| 6,181,766 B1 * | 1/2001 | Pearson, Jr. | A61B 6/56 | 378/15 |
| 6,185,271 B1 * | 2/2001 | Kinsinger | A61B 6/032 | 378/19 |
| 6,215,852 B1 * | 4/2001 | Rogers | H01J 35/105 | 378/141 |
| 6,229,870 B1 * | 5/2001 | Morgan | A61B 6/032 | 378/4 |
| 6,264,365 B1 * | 7/2001 | Patch | A61B 6/032 | 250/252.1 |
| 6,276,145 B1 * | 8/2001 | Sharpless | A61B 6/035 | 378/15 |
| 6,292,528 B1 * | 9/2001 | Wieczorek | A61B 6/032 | 250/363.02 |
| 6,507,642 B2 * | 1/2003 | Fujishige | A61B 6/06 | 378/150 |
| 6,687,326 B1 | 2/2004 | Bechwati et al. | | |
| 6,731,716 B2 * | 5/2004 | Mihara | A61B 6/032 | 378/147 |
| 6,975,699 B2 * | 12/2005 | Kresse | G01V 5/0016 | 378/19 |
| 7,016,459 B2 * | 3/2006 | Ellenbogen | G01N 23/046 | 378/19 |
| 7,027,554 B2 * | 4/2006 | Gaultier | G01T 1/2985 | 378/19 |
| 7,039,154 B1 * | 5/2006 | Ellenbogen | G01V 5/005 | 378/19 |
| 7,103,137 B2 * | 9/2006 | Seppi | G01N 23/04 | 378/57 |
| 7,106,825 B2 * | 9/2006 | Gregerson | G06T 11/005 | 378/19 |
| 7,108,421 B2 * | 9/2006 | Gregerson | A61B 6/032 | 378/146 |
| 7,123,681 B2 * | 10/2006 | Ellenbogen | G01N 23/046 | 378/19 |
| 7,164,747 B2 * | 1/2007 | Ellenbogen | G01N 23/046 | 378/19 |
| 7,224,765 B2 * | 5/2007 | Ellenbogen | G01N 23/046 | 378/19 |
| 7,236,560 B2 * | 6/2007 | Malamud | A61B 6/032 | 250/505.1 |
| 7,298,814 B2 * | 11/2007 | Popescu | A61B 6/032 | 378/19 |
| 7,352,841 B2 | 4/2008 | Ellenbogen et al. | | |
| 7,362,847 B2 * | 4/2008 | Bijjani | A61B 6/032 | 378/57 |
| 7,369,640 B2 | 5/2008 | Seppi et al. | | |
| 7,372,938 B2 * | 5/2008 | Pohan | G01T 1/1648 | 378/189 |
| 7,379,528 B2 * | 5/2008 | Mattson | G01N 23/046 | 250/370.09 |
| 7,391,845 B2 * | 6/2008 | Konno | A61B 6/032 | 250/208.1 |
| 7,430,282 B2 * | 9/2008 | Mori | A61B 6/032 | 378/145 |
| 7,440,537 B2 | 10/2008 | Ellenbogen et al. | | |
| 7,440,544 B2 * | 10/2008 | Scheinman | G01N 23/046 | 378/4 |
| 7,502,437 B2 | 3/2009 | Schlomka et al. | | |
| 7,526,064 B2 * | 4/2009 | Akery | G01N 23/04 | 378/198 |
| 7,545,905 B2 * | 6/2009 | Münker | G01N 23/046 | 378/20 |
| 7,551,714 B2 * | 6/2009 | Rothschild | G01N 23/046 | 378/44 |
| 7,672,422 B2 | 3/2010 | Seppi et al. | | |
| 7,778,383 B2 * | 8/2010 | Koehler | A61B 6/032 | 378/19 |

(56) References Cited

U.S. PATENT DOCUMENTS

| | | | |
|---|---|---|---|
| 7,792,239 B2* | 9/2010 | Nambu | A61B 6/032 378/19 |
| 7,852,981 B2* | 12/2010 | Luo | A61B 6/032 250/370.09 |
| 7,876,879 B2* | 1/2011 | Morton | G01T 1/2985 378/57 |
| 8,077,826 B2* | 12/2011 | Ruimi | A61B 6/032 378/19 |
| 8,111,804 B2* | 2/2012 | Dafni | A61B 6/032 378/16 |
| 8,135,110 B2 | 3/2012 | Morton | |
| 8,340,245 B2* | 12/2012 | Herranz | G01N 23/04 378/4 |
| 8,439,565 B2* | 5/2013 | Mastronardi | G01N 23/04 378/205 |
| 8,594,272 B2* | 11/2013 | Funk | A61B 6/032 378/10 |
| 8,744,211 B2* | 6/2014 | Owen | A61B 6/032 382/278 |
| 8,768,032 B2* | 7/2014 | Basu | G06T 11/005 250/559.05 |
| 8,774,351 B2* | 7/2014 | Funk | A61B 6/4488 378/62 |
| 8,831,305 B2* | 9/2014 | Zhang | A61B 6/032 382/128 |
| 8,873,705 B2* | 10/2014 | Konno | A61B 6/032 378/19 |
| 8,958,526 B2 | 2/2015 | Morton | |
| 8,971,484 B2* | 3/2015 | Beckmann | G01V 5/005 378/122 |
| 8,971,487 B2* | 3/2015 | Mastronardi | G01V 5/0008 378/57 |
| 9,000,382 B2* | 4/2015 | Mattson | G01T 1/00 250/363.01 |
| 9,044,152 B2* | 6/2015 | Abenaim | G01N 23/046 |
| 9,076,563 B2* | 7/2015 | Ying | A61B 6/032 |
| 9,078,569 B2* | 7/2015 | Ying | A61B 6/032 |
| 9,111,379 B2* | 8/2015 | Gregerson | G06T 11/003 |
| 9,119,589 B2* | 9/2015 | Zou | A61B 6/032 |
| 9,125,613 B2* | 9/2015 | Gregerson | A61B 6/4488 |
| 9,188,696 B2* | 11/2015 | Schafer | G01V 5/0016 |
| 9,217,794 B2* | 12/2015 | Morimoto | G01N 23/046 |
| 9,247,914 B2* | 2/2016 | Konno | A61B 6/032 |
| 9,285,327 B2* | 3/2016 | Ying | G01N 23/046 |
| 9,307,949 B2* | 4/2016 | Tsubota | A61B 6/032 |
| 9,314,220 B2* | 4/2016 | Luhta | A61B 6/56 |
| 9,395,313 B2* | 7/2016 | Pan | G01N 23/046 |
| 9,417,340 B2* | 8/2016 | Basu | G01T 1/2985 |
| 9,448,325 B2* | 9/2016 | Chen | A61B 6/032 |
| 9,453,937 B2* | 9/2016 | Zhang | G01T 1/2985 |
| 9,551,808 B2* | 1/2017 | Zhang | G01T 1/2985 |
| 2004/0017888 A1 | 1/2004 | Seppi et al. | |
| 2004/0120454 A1 | 6/2004 | Ellenbogen et al. | |
| 2005/0169422 A1 | 8/2005 | Ellenbogen | |
| 2005/0169423 A1 | 8/2005 | Ellenbogen et al. | |
| 2005/0249330 A1 | 11/2005 | Ellenbogen et al. | |
| 2006/0274879 A1 | 12/2006 | Ellenbogen et al. | |
| 2007/0003003 A1 | 1/2007 | Seppi et al. | |
| 2007/0133744 A1 | 6/2007 | Bijjani | |
| 2007/0147581 A1 | 6/2007 | Ellenbogen et al. | |
| 2007/0172022 A1 | 7/2007 | Schlomka et al. | |
| 2008/0205583 A1 | 8/2008 | Seppi et al. | |
| 2008/0304622 A1 | 12/2008 | Morton | |
| 2009/0060135 A1 | 3/2009 | Morton | |
| 2012/0134531 A1 | 5/2012 | Zhang et al. | |
| 2012/0230463 A1 | 9/2012 | Morton | |
| 2015/0378047 A1* | 12/2015 | Chen | G01V 5/0041 378/5 |
| 2017/0068017 A1* | 3/2017 | Zhao | G01V 5/0016 |

FOREIGN PATENT DOCUMENTS

| | | |
|---|---|---|
| CN | 101762613 A | 6/2010 |
| CN | 101788505 A | 7/2010 |
| CN | 101900695 A | 12/2010 |
| CN | 202041481 U | 11/2011 |
| CN | 202794067 | 3/2013 |
| CN | 202794067 U | 3/2013 |
| JP | S60-137350 A | 7/1985 |
| JP | H10-82747 A | 3/1998 |
| JP | 2005-534009 A | 11/2005 |
| JP | 2006-502386 A | 1/2006 |
| JP | 2007-528253 A | 10/2007 |
| JP | 2009-519471 A | 5/2009 |
| KR | 2005-0083718 A | 8/2005 |
| WO | WO 98/015817 A1 | 4/1998 |
| WO | WO 2004/031755 A2 | 4/2004 |
| WO | WO 2007/106674 A2 | 9/2007 |

OTHER PUBLICATIONS

State Intellectual Property Office of the People's Republic of China, International Search Report in International Application No. PCT/CN2013/079381 (dated Oct. 24, 2013).
State Intellectual Property Office of the People's Republic of China, Written Opinion in International Application No. PCT/CN2013/079381 (dated Oct. 24, 2013).
Australian Patent Office, Patent Examination Report No. 1 in Australian Patent Application No. 2013317476 (dated Jan. 8, 2016).
Japan Patent Office, Notification of Reasons for Refusal in Japanese Patent Application No. 2015-531431 (dated Jan. 26, 2016).
European Patent Office, Invitation Pursuant to Rule 62a(1) EPC in European Patent Application No. 13 839 779.9 (dated Apr. 11, 2016).
Wu et al., "Application of Computed Tomography in Explosives Detection," *CT Theory and Applications*, vol. 14, No. 1, pp. 24-32 (2005).
State Intellectual Property Office of the People's Republic of China, Office Action in Chinese Application No. 201210350516.X (dated May 25, 2015).
Korean Intellectual Property Office, Notification of Reason for Refusal in Korean Patent Application No. 10-2015-7009860 (dated May 17, 2016).
Australian Patent Office, Patent Examination Report No. 2 in Australian Patent Application No. 2013317476 (dated Jul. 7, 2016).
European Patent Office, Extended European Search Report in European Patent Application No. 13 839 779.9 (dated Jul. 15, 2016).

* cited by examiner

CT SECURITY INSPECTION SYSTEM FOR BAGGAGE AND DETECTOR ARRANGEMENT THEREOF

CROSS-REFERENCE TO RELATED APPLICATIONS

This application is the U.S. national phase of International Application No. PCT/CN2013/079381, filed on Jul. 15, 2013, which claims priority from and the benefit of Chinese Patent Application No. 201210350516.X, titled "CT Security Inspection System for Baggage and Detector Arrangement Thereof", filed on Sep. 19, 2012, the disclosures of which are incorporated herein by reference in their entirety.

BACKGROUND OF THE INVENTION

Technical Field

The present invention relates to a detector arrangement used in CT (computer tomography) security inspection system for baggage, and in particular, to a detector arrangement used in a rapid CT imaging technology for goods with small sizes, that allows a high scanning speed with the premise of optimal external dimension and profile of the apparatus. Also, the present invention relates to a CT security inspection system for baggage that includes the abovementioned detector arrangement.

Brief Description of Related Art

In the computer tomography scanning technology (hereafter referred to as "CT technology") based on X-ray radiation imaging, data for characteristic distribution of an object to be scanned in the tomography imaging is obtained by CT data reconstruction. Analysis of such characteristic data contributes to identification of common suspect substance in the baggage. In the field of security inspection for baggage, increased scanning speed and reduced occupied area, especially reduced width, of the security inspection are key factors that impact various applications of the CT technology in the field of security inspection.

Conventional CT apparatus includes X-ray source, collimating device, rotatable slip-ring, detection units, dedicated computer subsystem for data calculation, and, power and control subsystems, etc. Key factors that impacts CT performance and external dimension of this apparatus includes ray source, collimating device, and arrangement of the detection units. In these above factors, arrangement of the detection units determines directly width of the apparatus perpendicular to the direction of the scanning passage.

In configuration of the conventional CT apparatus, detection units are generally distributed in a circle centered at target of the ray source such that values P from simultaneous receipts of the ray beams by these detection units are so close to reduce the subsequent work such as algorithm processing. In addition, some detectors are manufactured in parts so that width of the apparatus is suitably reduced, however, this does not reduce the impact of arrangement of the detectors on the width of the apparatus. Also, since the detector crystals are mostly used in a sealed manner, manufacture of the detectors in parts causes data acquisitions and controls of the detector crystals to be performed by different control and acquisition modules, which leads to different acquisition timings and data transfer, thereby degrading the scanning speed of the CT apparatus.

SUMMARY

The present invention has been made to solve at least one of the abovementioned issues existing in the prior art.

Accordingly, it is an object of the present invention to provide a novel detector arrangement, around the scanning passage, for a CT system, which overcomes the technical bottleneck of miniature of the CT apparatus.

Accordingly, it is another object of the present invention to provide a novel CT security inspection system for baggage, which adopts the abovementioned detector arrangement that a plurality of detector units are arranged in the axial direction of the scanning passage, thereby achieving the rapid scanning as well as miniature of the apparatus.

According to one aspect of the present invention, there is provided a CT security inspection system for baggage, which has a miniature size and a rapid scanning speed. The CT security inspection system comprises a scanning passage through which a baggage enters and exits the CT security inspection system for baggage, an X-ray source provided at one side of the scanning passage, and, a gantry provided at an opposite side of the scanning passage and on which a plurality of detector units are mounted. In each of the detector units, a vertex point of at least one crystal receiving face is positioned in a detector unit distribution circle with its center at the center of the scanning passage. The detector units are arranged successively in which one is adjacent to another. All the detector crystal receiving faces of the plurality of detector units are within a scope of radiating ray beams with its center at a target of the X-ray source. In each of the detector units, a connection line between a midpoint of at least one of the detector crystal receiving faces and the target of the X-ray source is normal to the corresponding detector crystal receiving face.

In the abovementioned technical solution according to the present invention, in order to achieve the object to be solved by the CT technology (i.e., to obtain images by scanning the baggage to be scanned), gantry is arranged by centering the baggage scanning passage. The detector units are arranged, around the center of the scanning passage, on the gantry. With such arrangement, the CT security inspection system allows the rotating center of the slip-ring to be coincided substantially with the center of the arrangement of the detector units, such that rotating diameter of the rotatable CT slip-ring is reduced effectively, thereby reducing effectively final width for the apparatus.

Meanwhile, in order to ensure that all the detector crystal receiving faces are arranged to be normal to the ray beams emitted by the ray source, during assembling, each detector unit is arranged to be rotatable around the vertex point of the corresponding detector crystal receiving face, such that a connection line between the midpoint of the detector crystal receiving face on the corresponding detector unit and the target of the X-ray source is normal to the detector crystal receiving face on the corresponding detector unit, which achieves the integrated manufacturing of the gantry as well as improved sensitivity for data acquisition by the detector units. Data acquisition/control circuits are disposed in the same gantry, which improves the system availability while reducing impact caused by asynchrony of data acquisition.

Preferably, two or more detector crystals may be included in each detector unit in the axial direction of the scanning passage. The connection line between the midpoint of the detector crystal receiving face and the target of the X-ray source has a minimum angle, larger than 85°, with respect to the corresponding detector crystal receiving face, such that the impact of edge scattering onto the data acquired by the detectors is reduced.

Preferably, an emission angle of the X-ray source is at least larger than an angle between a connection line between the end of a head detector crystal and the target of the X-ray source and a connection line between the end of a tail detector crystal and the target of the X-ray source.

Preferably, an effective scanning region for the scanning passage is located within the scope of the angle between the connection line between the end of the head detector crystal and the target of the X-ray source and a connection line between the end of the tail detector crystal and the target of the X-ray source.

In a preferred embodiment, at least two detector crystals may be arranged in each detector unit. And, distance between every two adjacent detector crystals is related to belt delivery speed, rotation speed of the slip-ring and frequency of acquisition of the detector. Provided that the belt delivery speed is larger than 0.1 m/s and the rotation speed of the slip-ring is not less than 90 r/m, distance between every two adjacent detector crystals is not less than 20 mm/s.

Preferably, each of the detector units may comprise a support, a high density radiation-proof plate connected to the support, and, a plurality of detector crystals arranged on the high density radiation-proof plate and facing the X-ray source.

Preferably, the CT security inspection system may further comprise an acquisition module for acquiring signals from the detector units; a coding subsystem for recording the rotation angle of the slip-ring, and, an electrically control module for controlling radiation emission of the X-ray source and acquisition of the signals. The acquisition module and the control module are mounted within the same gantry.

Preferably, the CT security inspection system may further comprise first and second collimators each including a plurality of grids, for decomposing original ray emitted by the X-ray source into a plurality of fan ray beams.

Preferably, the CT security inspection system may further comprise a detector mounting plate on which a plurality of rows of detector crystals is mounted along an axial direction of the scanning passage. The decomposed fan ray beams correspond to the detector crystal receiving faces, respectively, so as to obtain synchronously a plurality of rows of tomography data for the baggage in the axial direction of the scanning passage.

Preferably, the grids for the first collimators may be embodied as one dotted fitting curves related to distribution of radiation dose, wherein slits between some of the grids in the middle are relatively narrow while slits between some of the grids in the margin are relatively broader. This may adjust radiation dose of the ray beams such that scopes of energy at locations where different detector crystal receiving faces are positioned may be substantially the same.

Preferably, the first collimator may include a plurality of grids in the belt delivery direction. Numbers of the grids and distances between the adjacent grids may be brought into correspondence with rows of the detectors and distances between the adjacent detector receiving faces in the belt delivery direction, respectively.

Preferably, in the detector units, the high density radiation-proof plate contains lead, W—Ni—Fe alloy, or steel.

Preferably, the grids of the collimators are formed with at least two slits.

Preferably, the CT security inspection system may further comprise a slip-ring subsystem disposed around the scanning passage, wherein the X-ray source and the gantry are mounted on the slip-ring subsystem and are rotatable about the center of the scanning passage.

According to the present invention, the X-ray source and the first collimator are mounted at the locations that correspond to the detector units in the CT scanning gantry. When an X-ray is emitted by the X-ray source, the first collimator decomposes the conical ray in the scanning region into a plurality of fan ray beams with certain coverage, wherein each fan ray beam corresponds to one detector crystal receiving face. Thus, when an X-ray is emitted by the X-ray source, the detectors may obtain simultaneously a plurality of X-ray beams transmitted through the tomography positions of the object to be scanned. Then, the x-ray signals accumulated in the detectors are transformed into electric signal, which is then transformed into digital signal by gain adjustment. Finally, by CT data reconstruction, data for characteristic distribution of the object to be scanned in different directions in the same tomography imaging is obtained.

With such arrangement, tomography data in different directions in several tomography positions may be obtained at the same time. In the specific CT security inspection apparatus, as distances between the target of the ray source and the detector crystal receiving faces are greatly larger than distance between the adjacent detector crystals, data acquired by the plurality of detector units may be regarded as the data in the corresponding adjacent tomography positions. That is, several sets of data can be obtained in one scanning such that the scanning speed of this CT apparatus is increased.

According to one aspect of the present invention, there is provided a detector arrangement used in a CT security inspection system for baggage. The CT security inspection system comprises a scanning passage through which a baggage enters and exits the CT security inspection system for baggage, an X-ray source provided at one side of the scanning passage, and a gantry provided at an opposite side of the scanning passage and on which a plurality of detector units are mounted. The detector arrangement comprises a plurality of detector units, wherein a vertex point of at least one detector crystal receiving face is positioned in a detector unit distribution circle with its center at a center of the scanning passage, and the detector units are arranged successively. All the detector crystal receiving faces of the plurality of detector units are within a scope of radiating ray beams with its center at a target of the X-ray source, and, in each of the detector units, a connection line between a midpoint of at least one of the detector crystal receiving faces and the target of the X-ray source is normal to the corresponding detector crystal receiving face.

In a preferred embodiment, dustproof shadow shield is mounted between the detector crystal receiving faces and the target of the X-ray source. Preferably, the dustproof shadow shield is made of light-weight material, including but not limited to Teflon, plastics, bakelite, and, aluminum foil.

Preferably, in each detector unit, a vertex point of at least one detector crystal receiving face is positioned in a detector unit distribution circle with its center at a center of the scanning passage, the connection line between the midpoint of at least one of the detector crystal receiving faces and the target of the X-ray source is normal to the corresponding detector crystal receiving face, and the plurality of detector units are arranged successively. All the detector crystal receiving faces are within the scope of radiating ray beams.

With the detector arrangement according to the present invention, since the angular relationship between the center of the scanning passage and the target of the X-ray source is determined, stability of values P reached on the detector crystal receiving faces can be obtained by data correction performed by the computer and thus the radiation intensity impact can be reduced.

BRIEF DESCRIPTION OF THE DRAWINGS

These and/or other aspects and advantages of the CT security inspection system for baggage according to embodiments of the present invention will become more apparent and more readily appreciated from the following description, taken in conjunction with the accompanying drawings of which.

Figure 1:
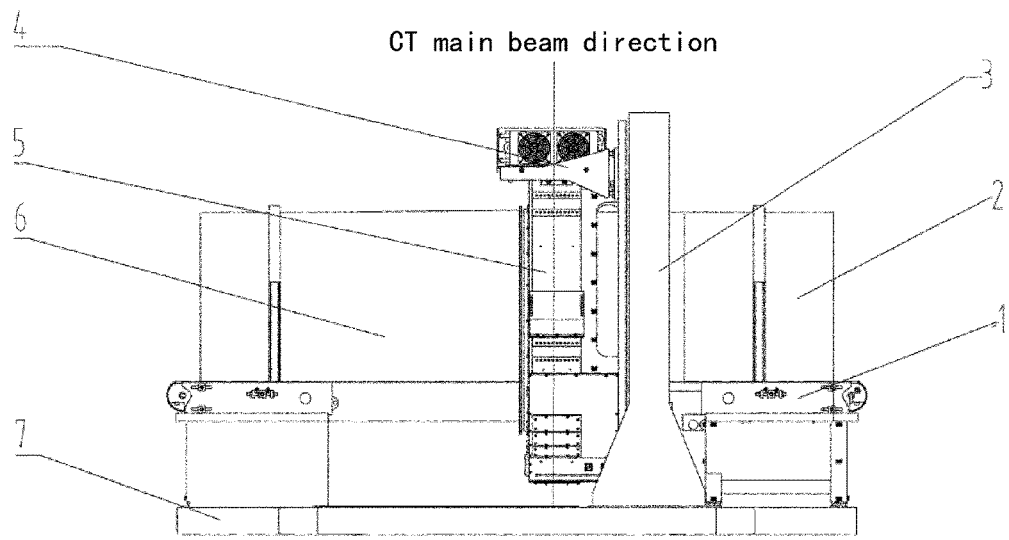
FIG. 1 is a schematic view of an overall CT security inspection system according to an embodiment of the invention.
Figure 2:
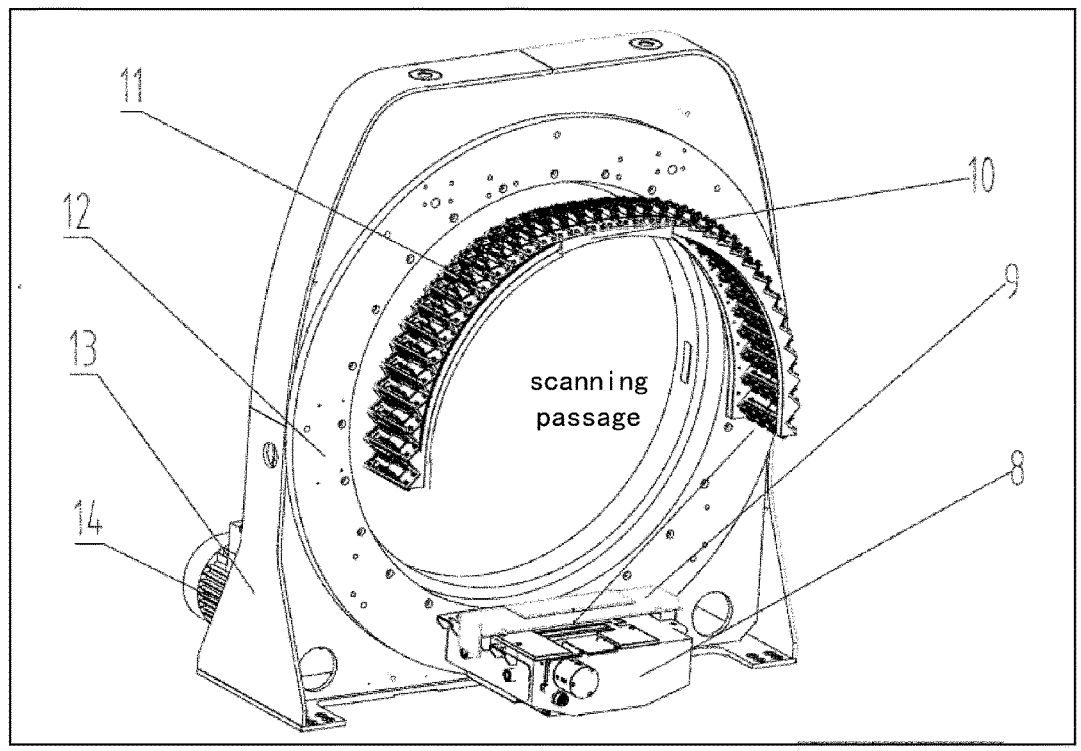
FIG. 2 is a schematic perspective view of main components of the CT security inspection system.

Explanations of these reference numbers.
1 belt delivery subsystem
2 entrance for scanning passage
3 slip-ring subsystem
4 support for X-ray source
5 gantry
6 exit for scanning passage
7 base plate for apparatus
8 CT X-ray source
9 first collimator
10 second collimator
11 detection region of the gantry
12 mounting plate of the gantry
13 support for slip-ring
14 slip-ring driving motor
15 target of X-ray source
16 head detector crystal receiving face
16A end of the head detector crystal
17 midpoint of the head detector crystal receiving face
18 vertex point of the head detector crystal receiving face
19 effective region for scanning passage
20 three detector units at the middle of the gantry
21 center of the scanning passage
22 detector unit distribution circle
23 vertex point of the tail detector crystal receiving face
24 tail detector crystal receiving face
25 midpoint of the tail detector crystal receiving face
25A end of the tail detector crystal
26 maximum angle between connection line between the detector crystal receiving face and the target for X-ray source and the corresponding detector crystal receiving face
27 detector crystal mounting bracket
28 high density radiation-proof plate
29 distance between adjacent detector crystals
30 detector crystal
31 internal support for detector units
32 detector crystal receiving face
33 detector unit mounting accessories
34 data acquisition/control module
35 detector mounting case
36 the detector unit's cross-sectional view
37 grids for second collimator
38 dustproof shadow shield
39 grids for first collimator
40 X-ray beam parallel to the scanning passage
41 attachment
42 attachment support

DETAILED DESCRIPTION OF EXEMPLARY EMBODIMENTS

Reference will now be made in detail to exemplary embodiments of the present specification, taken in conjunction with the accompanying drawings. It should be noted that the scope of the present invention will in no way be limited to components, steps and the relative arrangement thereof, numerical expressions and values, etc., set forth in these embodiments, unless otherwise specified. Meanwhile, it should be understood that, these figures in the accompanying drawings may not be drawn to scale, helping to description of the present invention. The following description is presented only by way of illustrations and possesses no limitations on applications and uses of the present invention. Known technologies, methods and apparatuses for those skilled in the art may be not discussed in detail, excluding, in some suitable situations, those seen as parts of the present specification. In these exemplary embodiments described and illustrated below, any specific values are explained only by way of representation and no limitations. Accordingly, different values may be adopted in alternative examples of these exemplary embodiments. It should be noted that like reference numbers and characters may have been used throughout these figures to denote like parts.

Referring to FIGS. 1-5, it shows a CT security inspection system for baggage according to an embodiment of the present invention. The CT security inspection system comprises a base plate 7 for apparatus, an entrance 2 for a scanning passage and an exit 6 for the scanning passage, and baggage (not shown) enters and exits the CT security inspection system for baggage through the scanning passage. An X-ray source 8 is provided on a support 4 for X-ray source 8 and between the entrance 2 and the exit 6 of the scanning passage. A gantry 5 is provided at an opposite side of the scanning passage, and a plurality of detector units 20 are mounted on the gantry 5. In each of the plurality of detector units 20, a vertex point 18 or 23 of at least one detector crystal receiving face is positioned in a detector unit distribution circle 22 with its center at a center 21 of the scanning passage, and the plurality of detector units 20 are arranged successively. All the detector crystal receiving faces 16 or 24 of the plurality of detector units 20 are within a scope of radiating ray beams with its center at a target 15 of the X-ray source 8. In each of the plurality of detector units 20, a connection line between a midpoint 17 or 25 of at least one of the detector crystal receiving faces 16 or 24 and the target 15 of the X-ray source 8 is normal to the corresponding detector crystal receiving face 16 or 24. As shown in FIGS. 1-5, in one preferred embodiment, the CT security inspection system further comprises a slip-ring subsystem 3 disposed around the scanning passage via an attachment 41 for attaching the scanning passage to the slip-ring, wherein the X-ray source 8 and the gantry 5 are mounted on the slip-ring subsystem 3 and are rotatable about the center 21 of the scanning passage.

Figure 3:
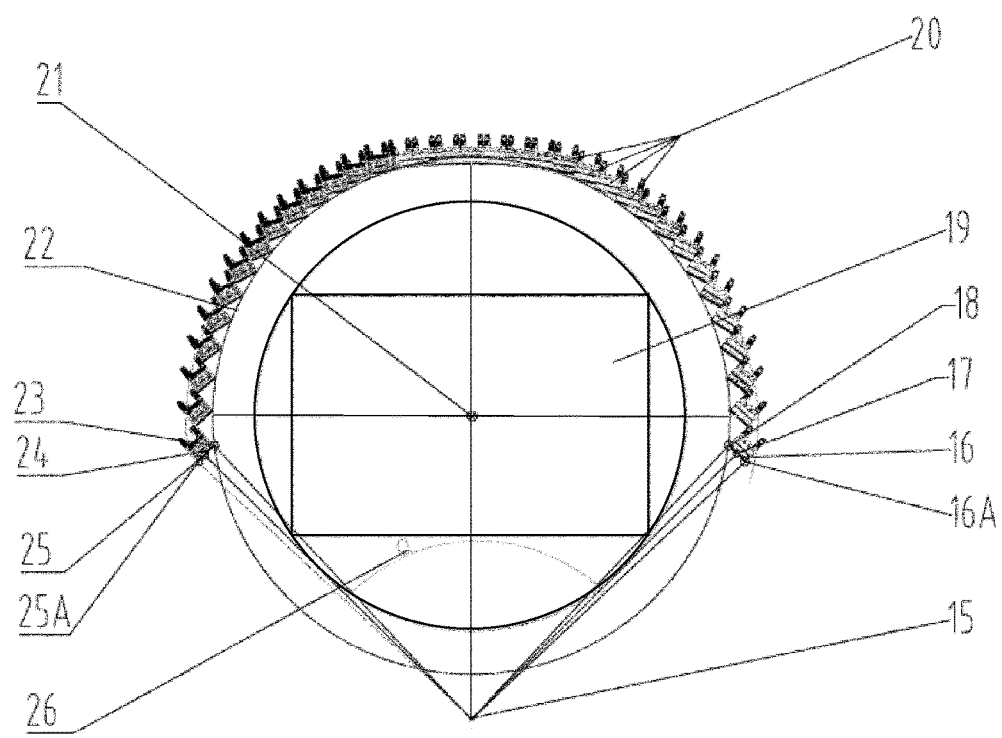
FIG. 3 is a schematic view of a detector arrangement perpendicular to a scanning passage.

As shown in FIG. 3, in each detector unit, a vertex point 18 or 23 of at least one detector crystal receiving face 16 or 24 is positioned in a detector unit distribution circle 22 with its center at the center 21 of the scanning passage, and the plurality of detector units 20 are arranged successively. All the detector crystal receiving faces 16 or 24 are positioned within the scope of the radiation ray beams with its center at the target 15 of the X-ray source 8. This optimal arrangement of the detector units 20 reduces width of the apparatus without reducing dimension of the scanning passage, so as to achieve reductions of the occupied area and of the cost.

As shown in FIGS. 1 and 3, in order to achieve imaging of the baggage to be scanned in the CT technology, the detector units 20 are provided on the gantry 5 such that they are arranged successively in a detector unit distribution circle 22 with its center at the center 21 of the scanning passage. In one example, a rotating center of the slip-ring subsystem 3 is coincided with center of the detector unit distribution circle 22 of the detector units 20, such that diameter of the rotatable CT slip-ring subsystem 3 (rotating object) is reduced effectively, so as to achieve minimum size for the apparatus under a rotatable CT condition.

Meanwhile, in order to ensure that all the detector crystal receiving faces 16 or 24 are arranged to be normal to the ray emitted by the X-ray source 8, during assembling, the detector crystal in each detector unit 20 is rotatable around the vertex point 18 or 23 of the corresponding detector crystal receiving face 16 or 24 as the pivot point at a certain angle, such that a connection line between the midpoint 17 or 25 of the at least one of the detector crystal receiving faces 16 or 24 on the detector units 20 and the target 15 of the X-ray source 8 is normal to the corresponding detector crystal receiving face 16 or 24 on the detector units 20, which achieves integrated manufacturing of the gantry 5. Data acquisition/control modules 34 for the plurality of detector units 20 are disposed in one gantry 5, which ensures accurate emission of the X-ray onto the detector crystal receiving faces 16 or 24 and enhances sensitivity of data acquisition by the plurality of detector units 20.

Figure 4:
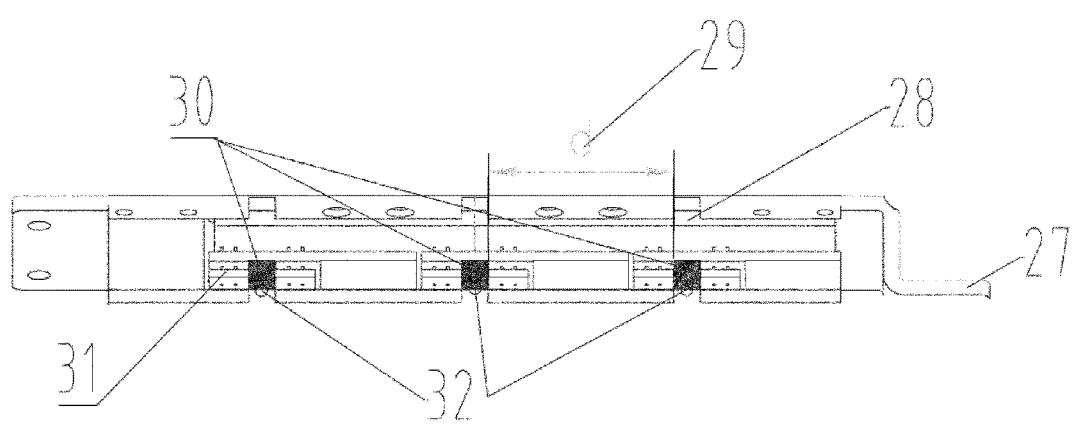
FIG. 4 is an enlarged schematic view showing details of the detector arrangement in FIG. 3.

As shown in FIGS. 3-4, according to the present invention, each detector unit 20 may include one or more detector crystal 30. The connection line between the midpoint of the detector crystal receiving face 32 and the target 15 of the X-ray source 8 has a minimum angle, equal to or larger than 85°, with respect to the corresponding detector crystal receiving face 32. Preferably, emission angle of the X-ray source 8 is at least larger than the angle 26 between the connection line between the end 16A of the head detector crystal and the target 15 of the X-ray source 8 and the connection line between the end 25A of the tail detector crystal and the target 15 of the X-ray source 8. Preferably, an effective scanning region 19 for the scanning passage is located within the scope of the angle between the connection line between the end 16A of the head detector crystal and the target 15 of the X-ray source 8 and the connection line between the end 25A of the tail detector crystal and the target 15 of the X-ray source 8.

With the abovementioned arrangement, a number of the detector units 20 within the detection region 11 on the gantry 5 is provided to cover the whole effective region 19 for the scanning passage such that drawback such as incomplete imaging is eliminated. Referring to FIGS. 1 and 3, during a CT scanning, upper surface of the belt delivery subsystem 1 must be positioned within the effective scanning region for the scanning passage such that baggage on the delivery belt can fall into the scanning region with coverage of the X-rays from the X-ray source 8. In addition, with such design, the detector crystal receiving face 32 of each detector crystal 30 is generally in line with the direction of the main beam of the X-ray such that amount of the effective radiation achieved by each detector crystal 30 is increased and scattering at the lateral of the detector crystal 30, so as to improve quality of the imaging in the CT apparatus.

As shown in FIGS. 1-5, in the abovementioned CT security inspection system, the gantry 5 is mounted on the rotatable mounting plate 12 of the gantry 5 in the slip-ring subsystem 3, and the mounting plate 12 of the gantry 5 is mounted on the support 13 for slip-ring and is driven by a slip-ring driving motor 14. Also, the detector units 20, the CT X-ray source 8 and the first collimator 9 and the second collimator 10 are mounted on the gantry 5. In this preferred embodiment, there is only one gantry 5 in this system. The gantry 5 is in a closed construction in which the data acquisition/control module 34 for data acquisition is mounted. Further, the acquired data can be processed by one type of algorithm, in order to increase the speed for performing a scanning operation in the CT security inspection system and the data transferring and processing speed.

As shown in FIGS. 3-4, two or more detector crystals 30 are arranged in each detector unit 20, and a distance 29 between every two adjacent detector crystals 30 is not less than 20 mm. Use of a plurality of detector crystals 30 obtains more data of the object to be scanned in one scanning, such that final pass rate and precision of recognition are improved. Further, each detector unit 20 may comprise a detector crystal mounting bracket 27, a high density radiation-proof plate 28 connected to the detector crystal mounting bracket 27, and, a detector crystal 30 arranged on internal support 31 for detector units 20 and facing the X-ray source 8. As shown, the high density radiation-proof plate 28 for the detector units 20 contains lead, W—Ni—Fe alloy, or steel, and has its thickness that satisfies requirements for environmental radiation leakage index required in industry standard.

Figure 5:
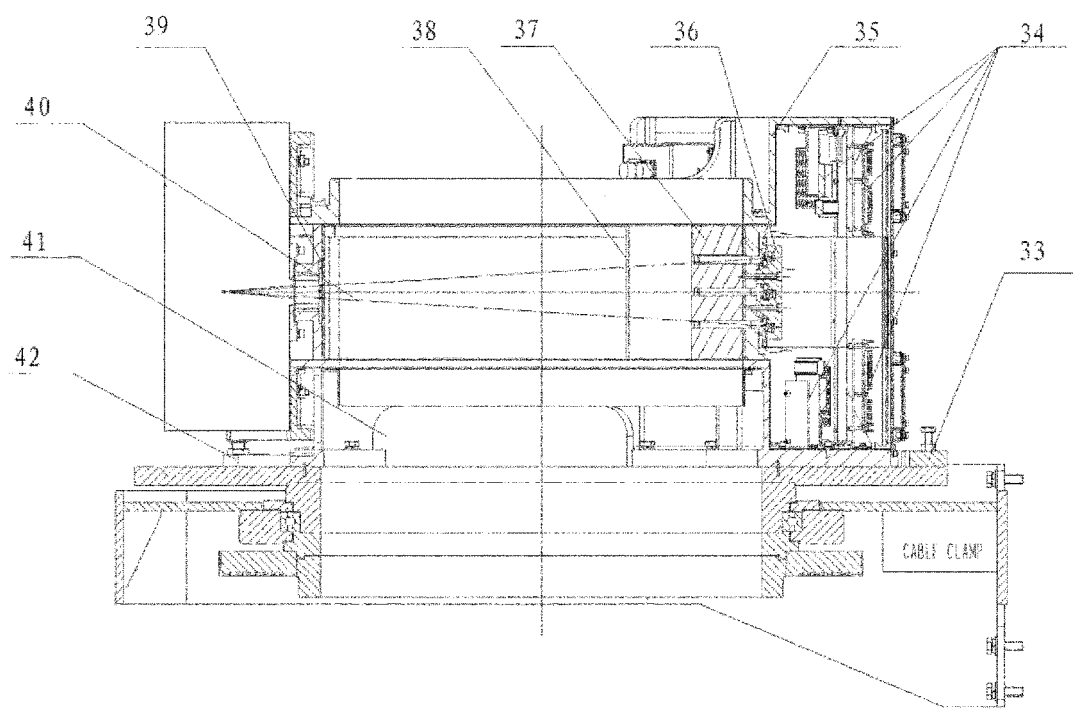
FIG. 5 is a schematic view showing construction of the detector arrangement in top view.

FIG. 5 is a schematic view showing construction of the detector arrangement in top view. The CT security inspection system for baggage further comprises a first collimator 9 and a second collimator 10. The first collimator 9 includes grids 39 for decomposing the X-rays emitted by the X-ray source 8 and controlling energy intensity of X-ray outputted therefrom. The second collimator 10 includes grids 37 for shielding the X-ray incident onto the detector units 20 such that the X-ray is incident onto the major area of the detector crystal receiving face 16 or 24, instead of being scattered by the margin of the detector crystal receiving face 16 or 24. As shown in FIGS. 1-5, the grids 39 for first collimator 9 include at least two partitions therein for decomposing the X-rays emitted by the X-ray source 8 into two or more fan ray beams. Further, as shown in FIGS. 3-4, along the direction of the scanning passage, a plurality of detector crystals 30 are mounted on the detector crystal mounting bracket 27. The decomposed fan ray beams correspond to these detector crystal receiving faces 16 or 24, respectively, to synchronously acquire the data from a plurality of detector units 20 along the direction of the scanning passage. FIG. 5 also shows the detector unit's cross-sectional view 36. The plurality of detector units 20 may be consisted of several detector crystal modules mounted within the detector mounting case 35 by the detector crystal mounting bracket 27. The detector mounting case 35 is sealed by detector unit mounting accessories 33 to reduce disturbance problems on the detector crystals 30 caused by the light, dust, and environmental humidity. The detector mounting case 35 is mounted on the CT gantry 5 by an attachment support 42. In order to reduce shielding of the ray beams in the main direction with the premise of sealing and shading, a dustproof shadow shield 38 is mounted at a position before the detector crystal receiving faces 16 or 24, towards the target 15 of the X-ray source 8. Preferably, the thickness is not greater than 3 mm. The dustproof shadow shield 38 is made of light-weight material, including but not limited to Teflon, plastics, bakelite, and, aluminum foil. In the preferred embodiment, the grids 39 and 37 of the collimators 9 and 10 are embodied as one or more dotted fitting curves related to distribution of radiation dose, wherein slits of some of the grids in the middle are relatively narrow while slits of some of the grids in the margin are relatively broader, such that scopes of energy at locations where different detector crystal receiving faces 16 or 24 are positioned are substantially the same. In this embodiment, the grid 39 for the first collimator 9 is provided with a plurality of slits, at least two, e.g., three shown in FIGS. 1-5.

Brief description on specific operation of this CT security inspection system for baggage according to the present invention will be introduced in the followings. Through the entrance 2 for scanning passage, baggage (no shown) is delivered into this CT security inspection system and meanwhile the light barrier at the entrance 2 is actuated, then, with the acquisition command issued by the data acquisition/control module 34, driven by the slip-ring driving motor 14, the gantry 5 starts to rotate together with rotation of the slip-ring subsystem 3. The X-ray emitted by the X-ray source 8 in the system passes through the first collimator 9 as frontier energy collimating device, and the latter decomposes the X-ray into several fan X-ray beams, for example, including an X-ray beam 40 parallel to the scanning passage, and then, the detector units 20 begin to acquire the data on these X-ray beams, and finally, by data processing, a 3D reconstruction is performed in order to obtain a CT image.

Although certain exemplary embodiments of the present invention have been shown and described, it will be appreciated by those skilled in the art that changes may be made in these exemplary embodiments without departing from the principles and spirit of the present invention, the scope of which is defined in the appended claims and their equivalents.

What is claimed is:

1. A CT security inspection system for baggage, the CT security inspection system comprising:
    a scanning passage, through which a baggage enters and exits the CT security inspection system for baggage;
    an X-ray source comprising a target provided at one side of the scanning passage;
    a plurality of detector units, wherein each detector unit of the plurality of detector units comprises one or more detector crystals; and
    a gantry provided at an opposite side of the scanning passage, and on which the plurality of detector units are mounted,
    wherein, in each detector unit of said plurality of detector units, a vertex point of at least one detector crystal receiving face of each detector crystal of the one or more detector crystals of each detector unit of the plurality of detector units is positioned in a detector unit distribution circle centered at a center of the scanning passage, and said plurality of detector units are arranged successively in which one is adjacent to another,
    wherein detector crystal receiving faces of each of said plurality of detector units are within a scope of radiating ray beams with their center at the target of the X-ray source, and, in each detector unit of said plurality of detector units, a connection line between a midpoint of at least one of the detector crystal receiving faces and the target of the X-ray source is normal to the corresponding detector crystal receiving face,
    wherein the connection line between the midpoint of the corresponding detector crystal receiving face and the target of the X-ray source relative to a plane where the corresponding detector crystal receiving face is located has a minimum angle, larger than 85°,
    wherein the plurality of detector units comprise a head detector unit and a tail detector unit, the head detector unit comprises a head detector crystal, and the tail detector unit comprises a tail detector crystal,
    wherein an emission angle of the X-ray source is at least larger than an angle between a connection line between the end of the head detector crystal and the target of the X-ray source and a connection line between the end of the tail detector crystal and the target of the X-ray source, and
    wherein an effective scanning region for the scanning passage is located within the scope of the angle between the connection line between the end of the head detector crystal and the target of the X-ray source and a connection line between the end of the tail detector crystal and the target of the X-ray source.

2. The CT security inspection system of claim 1, wherein at least two adjacent detector crystals are arranged in each detector unit of said plurality of detector units, and a distance between the at least two adjacent detector crystals is not less than 20 mm.

3. The CT security inspection system of claim 2, wherein each detector unit of said plurality of detector units comprises a support, a high density radiation-proof plate connected to the support, and, the at least two adjacent detector crystals arranged on the high density radiation-proof plate and facing the X-ray source.

4. The CT security inspection system of claim 3, further comprising:
    a first collimator and a second collimator, each including a plurality of grids, for decomposing original ray emitted by the X-ray source into a plurality of fan ray beams.

5. The CT security inspection system of claim 4, further comprising:
    a detector crystal mounting bracket on which the one or more detector crystals of each of the plurality of detector units are mounted along an axial direction of said scanning passage;
    wherein said plurality of fan ray beams decomposed correspond to the detector crystal receiving faces, respectively, so as to obtain a plurality of detecting data synchronously in the axial direction of said scanning passage.

6. The CT security inspection system of claim 4, wherein the plurality of grids for the first collimator and the second collimator comprise one or more dotted fitting curves related to distribution of radiation dose, wherein slits between some of the plurality of grids in the middle are relatively narrow while slits between some of the plurality of grids in the margin are relatively broader, such that scopes of energy at locations where different detector crystal receiving faces are positioned are substantially the same.

7. The CT security inspection system of claim 6, wherein the plurality of grids of the first collimator and the second collimator comprise at least two slits.

8. The CT security inspection system of claim 3, wherein said high density radiation-proof plate contains lead, W—Ni—Fe alloy, or steel.

9. The CT security inspection system of claim 1, further comprising a slip-ring subsystem disposed around said scanning passage, wherein said X-ray source and said gantry are mounted on the slip-ring subsystem and are rotatable about said center of the scanning passage.

10. A detector arrangement used in a CT security inspection system for baggage, the CT security inspection system comprising:
- a scanning passage, through which a baggage enters and exits the CT security inspection system for baggage;
- an X-ray source comprising a target provided at one side of the scanning passage;
- a gantry provided at an opposite side of the scanning passage; and
- a first collimator and a second collimator each including a plurality of grids for decomposing the original ray from the X-ray source into a plurality of fan ray beams,
- wherein the detector arrangement comprises:
  - a plurality of detector units, wherein each detector unit of the plurality of detector units comprises one or more detector crystals, wherein a vertex point of at least one detector crystal receiving face of a detector crystal of each of the one or more detector crystals of each detector unit of the plurality of detector units is positioned in a detector unit distribution circle with its center at a center of the scanning passage, and said plurality of detector units are arranged successively; and
  - wherein detector crystal receiving faces of each of the plurality of detector units are within a scope of radiating ray beams with their center at the target of the X-ray source, and, in each detector unit of said plurality of detector units, a connection line between a midpoint of at least one of the detector crystal receiving faces and the target of the X-ray source is normal to the corresponding detector crystal receiving face.

11. The detector arrangement of claim 10, wherein the connection line between the midpoint of the corresponding detector crystal receiving face and the target of the X-ray source relative to a plane where the corresponding detector crystal receiving face is located has a minimum angle, equal to or larger than 85°.

12. The detector arrangement of claim 11, wherein, the plurality of detector units comprise a head detector unit and a tail detector unit, the head detector unit comprises a head detector crystal, and the tail detector unit comprises a tail detector crystal; and
- wherein an emission angle of the X-ray source is at least larger than an angle between a connection line between the end of the head detector crystal and the target of the X-ray source and a connection line between the end of the tail detector crystal and the target of the X-ray source.

13. The detector arrangement of claim 12, wherein an effective scanning region for the scanning passage is located within a scope of the angle between the connection line between the end of the head detector crystal and the target of the X-ray source and a connection line between the end of the tail detector crystal and the target of the X-ray source.

14. The detector arrangement of claim 10, further comprising a dustproof shadow shield mounted between the detector crystal receiving faces and the target of the X-ray source for shielding visible light from impinging on the detector crystal receiving face and preventing foreign matters from accumulating on the detector crystal receiving face, wherein the dustproof shadow shield is made of light-weight material, including but not limited to polytetrafluoroethylene, plastics, bakelite and aluminum foil.

15. A CT security inspection system for baggage, the CT security inspection system comprising:
- a scanning passage, through which a baggage enters and exits the CT security inspection system for baggage;
- an X-ray source comprising a target provided at one side of the scanning passage;
- a plurality of detector units, wherein each detector unit of the plurality of detector units comprises one or more detector crystals;
- a gantry provided at an opposite side of the scanning passage, and on which the plurality of detector units are mounted; and
- a first collimator and a second collimator, each including a plurality of grids for decomposing an original ray from the X-ray source into a plurality of fan ray beams,
- wherein, in each detector unit of said plurality of detector units, a vertex point of at least one detector crystal receiving face of each detector crystal of the one or more detector crystals of each detector unit of the plurality of detector units is positioned in a detector unit distribution circle centered at a center of the scanning passage, and said plurality of detector units are arranged successively in which one is adjacent to another, and
- wherein detector crystal receiving faces of each of said plurality of detector units are within a scope of radiating ray beams with their center at the target of the X-ray source, and, in each detector unit of said plurality of detector units, a connection line between a midpoint of at least one of the detector crystal receiving faces and the target of the X-ray source is normal to the corresponding detector crystal receiving face.

16. The CT security inspection system of claim 15, wherein the connection line between the midpoint of the corresponding detector crystal receiving face and the target of the X-ray source relative to a plane where the corresponding detector crystal receiving face is located has a minimum angle, larger than 85°.

17. The CT security inspection system of claim 16, wherein the plurality of detector units comprise a head detector unit and a tail detector unit, the head detector unit comprises a head detector crystal, and the tail detector unit comprises a tail detector crystal, and
- wherein an emission angle of the X-ray source is at least larger than an angle between a connection line between the end of the head detector crystal and the target of the X-ray source and a connection line between the end of the tail detector crystal and the target of the X-ray source.

18. The CT security inspection system of claim 17, wherein an effective scanning region for the scanning passage is located within the scope of the angle between the connection line between the end of the head detector crystal and the target of the X-ray source and a connection line between the end of the tail detector crystal and the target of the X-ray source.

19. The CT security inspection system of claim 15, further comprising a slip-ring subsystem disposed around said scanning passage, wherein said X-ray source and said gantry are mounted on the slip-ring subsystem and are rotatable about said center of the scanning passage.

* * * * *